United States Patent
Ito (10) Patent No.: US 8,139,296 B2
(45) Date of Patent: Mar. 20, 2012

(54) REIMAGING OPTICAL SYSTEM AND ENDOSCOPE USING THE SAME

(75) Inventor: Koichiro Ito, Shibuya-Ku (JP)

(73) Assignee: Olympus Medical Systems Corp., Tokyo (JP)

( * ) Notice: Subject to any disclaimer, the term of this patent is extended or adjusted under 35 U.S.C. 154(b) by 472 days.

(21) Appl. No.: 12/368,954

(22) Filed: Feb. 10, 2009

(65) Prior Publication Data
US 2009/0203963 A1    Aug. 13, 2009

(30) Foreign Application Priority Data
Feb. 12, 2008    (JP) ................... 2008-029967

(51) Int. Cl.
    G02B 9/64     (2006.01)
    G02B 21/36    (2006.01)
    G02B 23/00    (2006.01)
    H04N 7/18     (2006.01)

(52) U.S. Cl. .................... 359/755; 359/363; 348/65

(58) Field of Classification Search ................. 359/363, 359/368, 676, 755; 348/65, 69, 76
See application file for complete search history.

(56) References Cited

U.S. PATENT DOCUMENTS
7,649,681 B2 * 1/2010 Hauger et al. ............... 359/363
7,800,830 B2 * 9/2010 Mihara ........................ 359/676

FOREIGN PATENT DOCUMENTS
JP    2003-084214    3/2003

* cited by examiner

Primary Examiner — Alicia M Harrington
(74) Attorney, Agent, or Firm — Arnold International; Bruce Y. Arnold (57) ABSTRACT

The invention relates to an reimaging optical system that has a sufficiently enhanced magnification and better performance, and an endoscope using the same. The reimaging optical system 3 is adapted to re-form an image by an image guide 6 on a solid-state imaging device 4 having a diagonal length of 6.5 mm or longer, and satisfies the following condition.

$$0.6 < (D \times |\beta|)/V \quad (1).$$

Here D is the diameter of the image guide 6, $\beta$ is the optical transverse magnification of the reimaging optical system 3, and V in mm is the minor axis direction length of an imaging area of the solid-state imaging device 4.

8 Claims, 9 Drawing Sheets

FIG. 1

Example 1

FIG. 2

Example 2

FIG. 3

Example 3

FIG. 4

Example 4

FIG. 5

Example 5

FIG. 6

Example 1

FIG. 7

Example 2

FIG. 8

Example 3

FIG. 9

Example 4

FIG. 10

Example 5

REIMAGING OPTICAL SYSTEM AND ENDOSCOPE USING THE SAME

BACKGROUND OF THE INVENTION

The present invention relates to a reimaging optical system adapted to re-form an image formed by an image guide on a solid-state imaging device, and an endoscope using the same.

In recent years, as endoscope systems are used in steadily expanding applications, there is rising expectation that they could be used in medical fields, e.g., for ordinary medical practices such as clearing up of phlegm from phlegm-stricken patients in wards, tracheal tube position checking in operating or treatment rooms for the purpose of maintenance of an airway before and after operations, and examination of non-resident patients.

Conventional heavy, bulky endoscope systems have difficulty carrying around and getting hold of positions after movement, and there is expectation that they could easily be carried around.

With a typical prior art portable endoscope having an end face of an image guide located on an imaging position, the formed image was guided through the image guide to a base end side of an insert so that an operator could examine sites under observation by way of an eyepiece optical system of an eyepiece portion. A problem with this was, however, that the operator was usually limited to a single person; the images could not been observed by two or more at the same time.

One possible approach to solving that problem is to use a digital camera's CCD and LCD so that an image by the image guide is formed on the CCD and viewed it through the LCD. With this approach, there can be an easy-to-carry endoscope set up that enables images to be observed by two or more.

Among reimaging optical systems so for known in the art, there is an optical system set forth in Patent Publication 1.

[Patent Publication 1]
JP(A)2003-84214

With the reimaging optical system of Patent Publication 1, however, an image by image fibers (on the end face of a bundle of image guide fibers) is hardly formed on a CCD that is generally used on a digital camera and has a diagonal length of 6.5 mm or longer. This is because the transverse magnification of a reimaging optical system adapted to form an image by the image fibers (the end face of the bundle of the image guide fibers) on the imaging area of the CCD is insufficient for this purpose. Even when the image by the image fibers is electrically enlarged, there are more noises and image quality deterioration that may otherwise interfere with observation.

SUMMARY OF THE INVENTION

Having been made with such problems as mentioned above in mind, the invention has for its object the provision of a reimaging optical system having adequately improved magnifications and better performance, and an endoscope using it.

According to the invention, the aforesaid object is accomplishable by the provision of a reimaging optical system adapted to re-form an image by an image guide on a solid-state imaging device having a diagonal length of 6.5 mm or longer, characterized by satisfying the following condition:

$$0.6 < (D \times |\beta|)/V \quad (1); \text{ and}$$

where D is the diameter of said image guide, $\beta$ is the optical transverse magnification of said reimaging optical system, and V in mm is the minor axis direction length of an imaging area of said solid-state imaging device.

Condition (1) is provided to define the optical transverse magnification of the reimaging optical system. As the lower limit of 0.6 to condition (1) is not reached, it interferes with observation because smaller images are going to be formed relative to the solid-state imaging device having a diagonal length of 6.5 mm or longer. Also, when the images are electrically enlarged, there are more noises and image quality deterioration that again interfere with observation.

It is desired that the aforesaid reimaging optical system comprise a front unit, a stop and a rear unit, and satisfy the following condition (2):

$$1 < f_F/F \quad (2)$$

where $f_F$ is the focal length of the front unit, and F is the focal length of the whole reimaging optical system.

Condition (2) relates to the combined power of the front unit. For generally available imaging optical systems, it is demanded to obtain bright images, and so fibers having an NA of 0.1 or more are often used as image guide fibers. It is then desired to satisfy condition (2). As the lower limit of 1 to condition (2) is not reached and the focal length of the front unit becomes short, it gives rise to increased spherical aberrations, resulting in poorer imaging capability.

It is more desired to satisfy the following condition:

$$f_F/F < 2.5 \quad (2)'$$

As the upper limit of 2.5 to condition (2)' is exceeded and the focal length of the front unit grows long, it gives rise to increased spherical aberrations, resulting in poorer imaging capability.

For the aforesaid front unit, it is desired to comprise a first lens group including at least one positive single lens and a second lens group including a cemented lens of a positive lens and a negative lens, and satisfy the following condition:

$$0.9 < f_{2P}/F \quad (3)$$

where $f_{2P}$ is the focal length of the positive lens in the second lens group.

Condition (3) relates to the power of the positive lens in the second lens group. As the lower limit of 0.9 to condition (3) is not reached, it gives rise to increased spherical aberrations.

It is more desired to satisfy the following condition:

$$F_{2P}/F < 3 \quad (3)'$$

As the upper limit of 3 to condition (3)' is exceeded and the focal length of the positive lens in the second lens group grows long, it causes the power of the first lens group to grow strong, resulting in increased coma and spherical aberrations and, hence, imaging capability deterioration.

For the aforesaid reimaging optical system, it is desired to comprise a front unit, a stop and a rear unit, and satisfy the following condition:

$$6 < |f_B|/f_F \quad (4)$$

where $f_F$ is the focus length of the front unit, and $f_B$ is the focal length of the rear unit.

Condition (4) relates to the power profile of the front and rear units. As the lower limit of 6 to condition (4) is not reached, there is difficulty making sure the necessary magnification, and there are increased spherical aberrations as well, resulting in imaging capability deterioration.

In the aforesaid reimaging optical system, it is desired that an optical low-pass filter be located on the side of the aforesaid image guide.

When images are formed on the solid-state imaging device at high magnifications, dots in the image fibers forming the image guide are enlarged and imaged: they are going to stand very conspicuous. For dot removal, it has been known to use an optical low-pass filter. Generally, the optical low-pass filter is inserted on the solid-state imaging device side; however, when used with an optical system likely to have high magnifications, there is inconvenience that it grows too thick, and too long in the whole length. If the optical low-pass filter is located on the image guide side, its full length is prevented from growing long while the effect on dot removal is ensured.

To achieve the aforesaid object, the inventive endoscope is characterized by comprising an objective lens located at an end of the endoscope, an image guide for guiding an object image formed by said objective lens, and a reimaging optical system adapted to re-form the object image guided by said image guide on a solid-state imaging device having a diagonal length of 6.5 mm or longer, wherein said reimaging device is any one of such reimaging optical systems as described above.

It is desired that the aforesaid endoscope is provided with an illumination means comprising a white light emitting diode, and be free of any color correction filter.

It is also desired that said white light emitting diode be at a color temperature of 4,600 K or higher.

Figure 11:
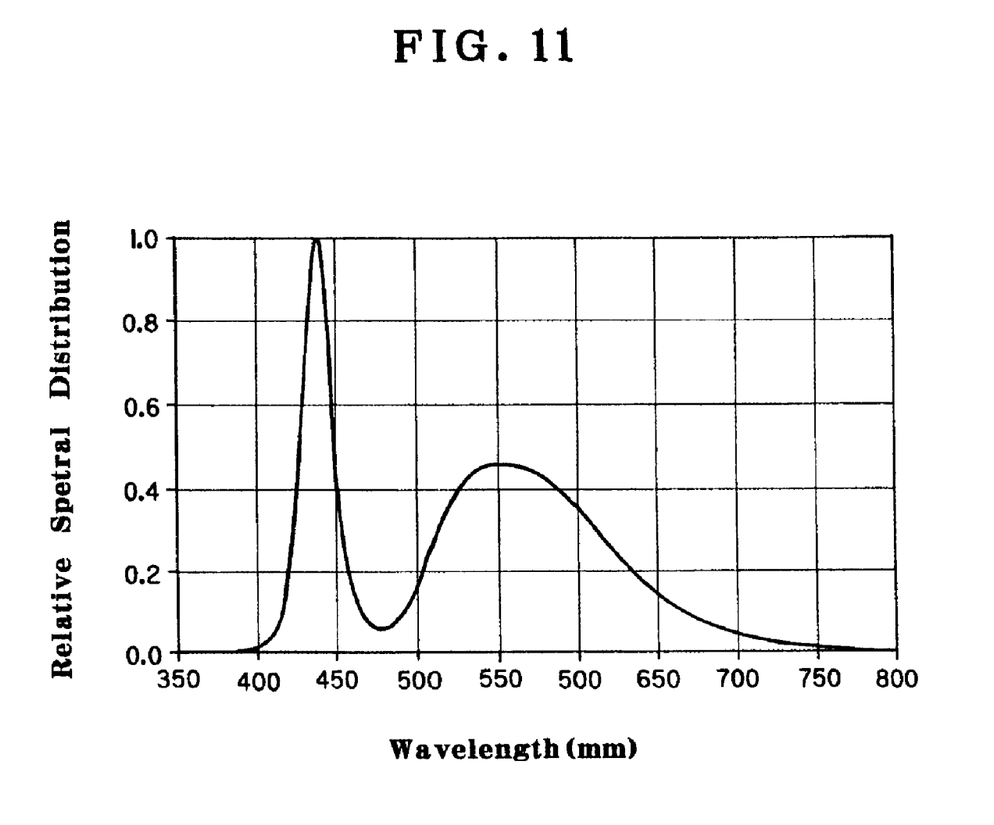
FIG. 11 is indicative of one example of the spectral characteristics of the white light emitting diode.

As the white light emitting diode is used as the light source, there is no need of providing another light source, resulting in an improvement in the carryability of the endoscope. The white light emitting diode creates white light by mixing excited light having a wavelength of around 450 nm with fluorescence of around 500 nm to 630 nm, and has such spectral characteristics as shown in FIG. 11 as an example. It follows that the spectra from the light emitting diode contain less red but more blue in itself. For this reason, there is better color reproduction rather without recourse to any color correction filter, which in turn contributes more to part counts reductions. Better color reproduction is also achieved at a color temperature of 4,600 K or higher.

For the aforesaid endoscope, it is desired to have a display means adapted to show images based on electric signals from the aforesaid solid-state imaging device.

If a display monitor is integral with the endoscope, the carry ability of the endoscope is more improved.

As described above, the present invention provides a reimaging optical system designed to re-form images by an image guide on a solid-state imaging device having a diagonal length of 6.5 mm or longer, which has adequately improved magnifications and better performance, and an endoscope using the same as well.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Some embodiments of the inventive reimaging optical system and the endoscope using the same are now explained with reference to the accompanying drawings and exemplary data.

EXAMPLE 1

Figure 1:
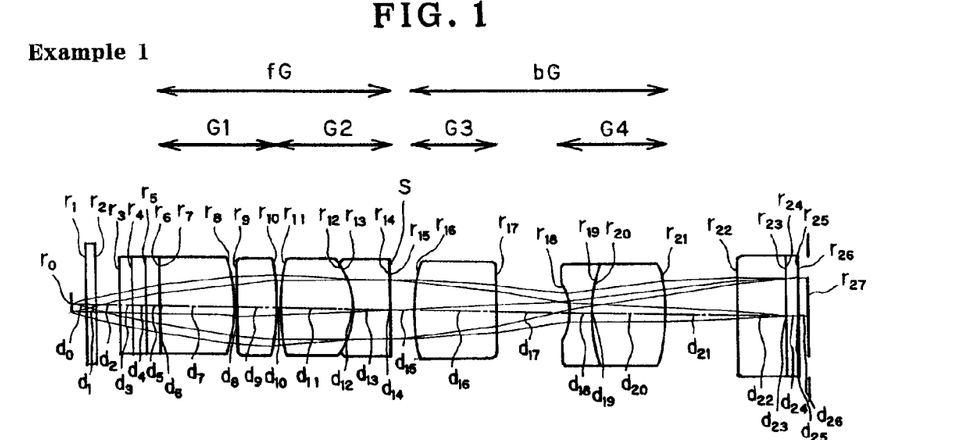
FIG. 1 is illustrative in lens arrangement of the reimaging optical system according to Example 1 of the invention.
Figure 6:
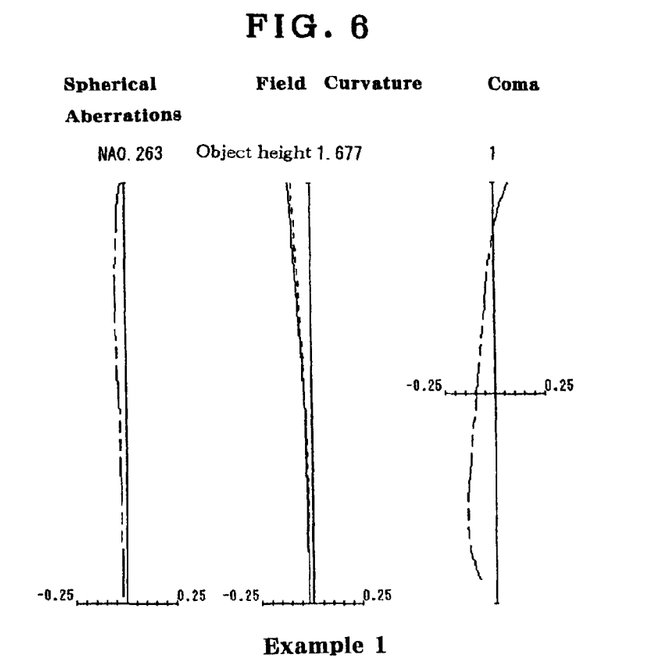
FIG. 6 is an aberration diagram for Example 1.

FIG. 1 is illustrative in lens arrangement of the reimaging optical system according to Example 1 of the invention, and FIG. 6 is an aberration diagram for Example 1. Note here that throughout the disclosure, length is given in mm. As shown in FIG. 1, the reimaging optical system here is built up of a front unit fG located on the object side of a stop S and a rear unit bG located on the image side of the stop S. The front unit fG is made up of two plano-convex positive lenses, each convex on its image side, and a cemented lens of a double-convex positive lens and a negative lens concave on its object side; two such plano-convex positive lenses form a first group G1, and the cemented lens of a double-convex positive lens and a negative lens concave on its object side forms the second group G2. The rear unit bG is made up of a convex-plano positive lens convex on its object side and a cemented lens of a double-concave negative lens and a double-convex positive lens; the convex-plano positive lens forms the third group G3 and the cemented lens of a double-concave negative lens and a double-convex positive lens forms the fourth group G4. Thus, the lens arrangement here comprises four groups or seven lenses. A triplet optical low-pass filter is located on the object side of the front unit fG, and the effective imaging range of the imaging device here is supposed to be 5.77 mm×4.34 mm.

Numerical data about the optical members that form the reimaging optical system of Example 1 will be given later. Surface numbers counted from the object plane, radius of curvature, surface-to-surface spacing or air spacing, refractive index and Abbe constant are indicated by "No", "r", "d", "ne" and "ve", respectively. The refractive index ne and Abbe constant ve are given on an e-line basis. Note here that ve= $(ne-1)/(n_{F'}-n_{C'})$ where $n_{F'}$ is the F'-line refractive index and $n_{C'}$ is the C'-line refractive index. The same shall go for the following examples.

In FIG. 1, note that optical surface Nos. 1, 2, 3, . . . are indicated by $r_1, r_2, r_3, \ldots$, and spaces or air spaces between surface Nos. 1 and 2, 2 and 3, 3 and 4, . . . are indicated by $d_1, d_2, d_3, \ldots$.

Parameters for the conditions in the example here are given below.

| Parameters | Symbol | Unit | Value |
|---|---|---|---|
| Image guide's diameter | D | [mm] | 0.8 |
| Optical transverse magnification | β | | −4.141 |
| Minor-axis direction length of the imaging device | V | [mm] | 4.34 |
| Focal length of the front unit | $f_F$ | [mm] | 4.381 |
| Focal length of the whole system | F | [mm] | 3.301 |
| Focal length of the positive lens in the second lens group | $f_{2P}$ | [mm] | 3.763 |
| Focal length of the rear unit | $f_B$ | [mm] | 66.015 |

In the example here, there are three optical low-pass filters placed on the object side of the reimaging optical system, and the total thickness of them is 1.68 mm. When they are placed on the image side, there is the required thickness given by optical transverse magnification β×1.68=6.96 mm: too long a whole length.

EXAMPLE 2

Figure 2:
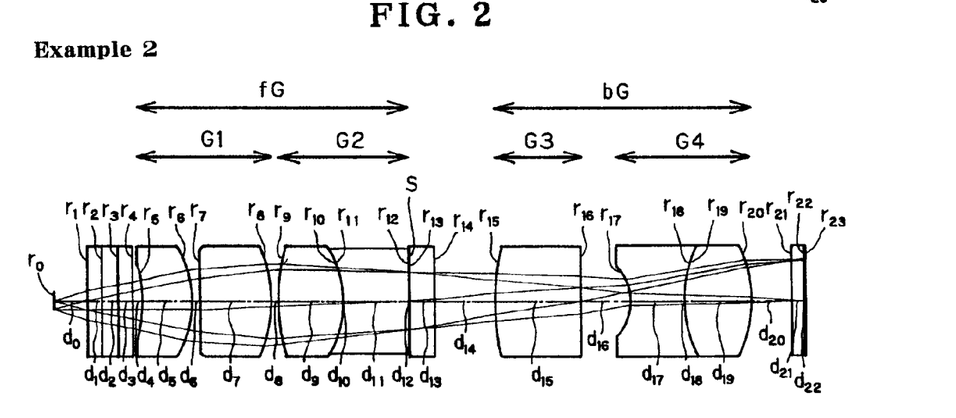
FIG. 2 is illustrative in lens arrangement of the reimaging optical system according to Example 2 of the invention.
Figure 7:
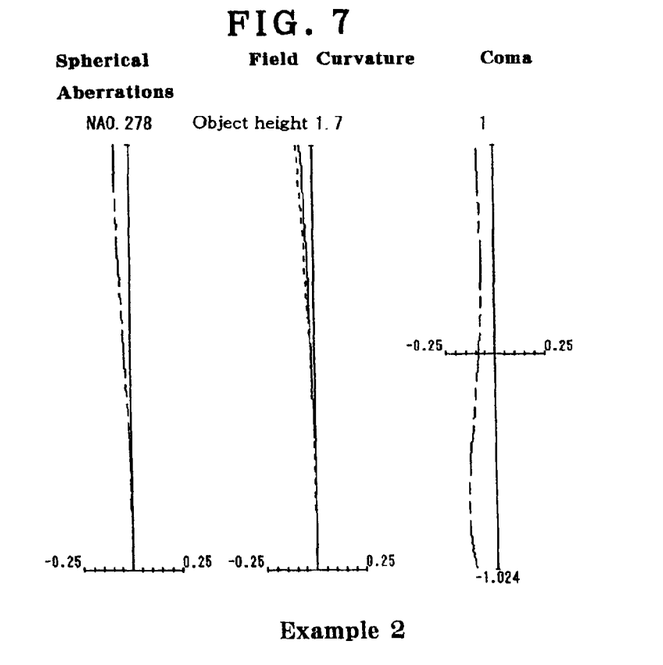
FIG. 7 is an aberration diagram for Example 2.

FIG. 2 is illustrative in lens arrangement of the reimaging optical system according to Example 2 of the invention, and FIG. 7 is an aberration diagram for Example 2. As shown in FIG. 2, the reimaging optical system here is built up of a front unit fG located on the object side of a stop S and a rear unit bG located on the image side of the stop S. The front unit fG is made up of a positive meniscus lens concave on its object side, a plano-convex positive lens convex on its image side and a cemented lens of a double-convex positive lens and a negative lens concave on its object side; the positive meniscus lens and plane-convex positive lens form the first group G1, and the cemented lens of a double-convex positive lens and a negative lens concave on its object side form the second group G2. The rear unit bG is made up of a plane-convex positive lens convex on its object side and a cemented lens of a double-concave negative lens and a double-convex positive lens; the convex-plano positive lens forms the third group G3, and the cemented lens of a double-concave negative lens and a double-convex positive lens forms the fourth lens group G4. Thus, the lens arrangement here comprises four groups or seven lenses. A triplet optical low-pass filter is located on the object side of the front unit fG, and the effective imaging range of the imaging device is supposed to be 5.77 mm×4.34 mm. In the example here, an infrared cut filter is located just after the stop S. When light in the infrared range offers a problem with color reproduction, such an infrared cut filter could be used.

Numerical data on the optical members that form the reimaging optical system of Example 2 will be given later.

Parameters for the conditions in the example here are given just below.

| Parameters | Symbol | Unit | Value |
|---|---|---|---|
| Image guide's diameter | D | [mm] | 0.8 |
| Optical transverse magnification | β | | −4.175 |
| Minor-axis direction length of the imaging device | V | [mm] | 4.34 |
| Focal length of the front unit | $f_F$ | [mm] | 4.367 |
| Focal length of the whole system | F | [mm] | 3.937 |
| Focal length of the positive lens in the second lens group | $f_{2P}$ | [mm] | 4.047 |
| Focal length of the rear unit | $f_B$ | [mm] | −26.701 |

EXAMPLE 3

Figure 3:
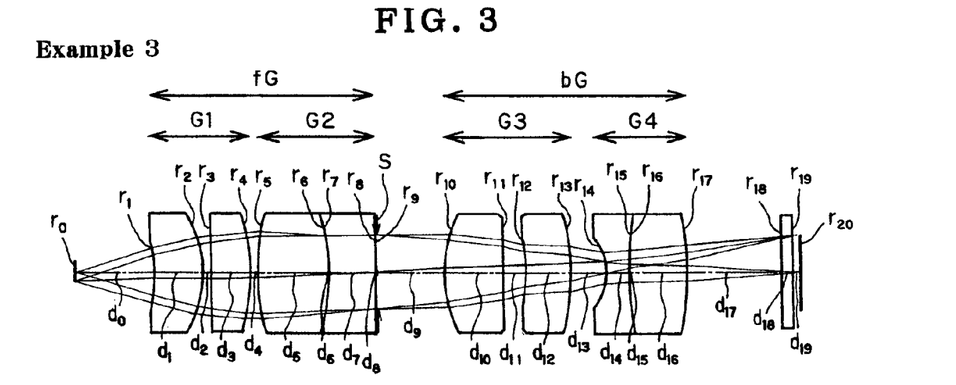
FIG. 3 is illustrative in lens arrangement of the reimaging optical system according to Example 3 of the invention.
Figure 8:
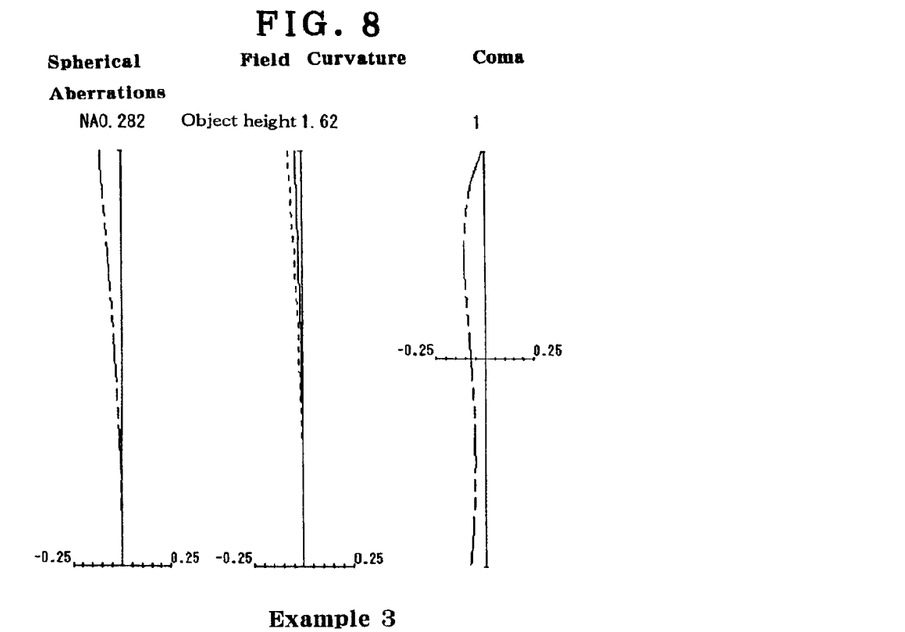
FIG. 8 is an aberration diagram for Example 3.

FIG. 3 is illustrative in lens arrangement of the reimaging optical system according to Example 3 of the invention, and FIG. 8 is an aberration diagram for Example 3. As shown in FIG. 3, the reimaging optical system here is built up of a front unit fG located on the object side of a stop S and a rear unit bG located on the image side of the stop S. The front unit fG is made up of a positive meniscus lens concave on its object side, a plano-convex positive lens convex on its image side and a cemented lens of a double-convex positive lens and a negative lens concave on its object side; the positive meniscus lens and plano-convex positive lens form the first group G1, and the cemented lens of a double-convex positive lens and a negative lens concave on its object side form the second group G2. The rear unit bG is made up of a convex-plano positive lens convex on its object side, a positive meniscus lens convex on its image side and a cemented lens of a double-concave negative lens and a double-convex positive lens; the convex-plano positive lens and positive meniscus lens form the third group G3, and the cemented lens of a double-concave negative lens and a double-convex positive lens forms the fourth group G4. Thus, the lens arrangement here comprises four groups or eight lenses. The effective imaging range of the imaging device is supposed to be 5.33 mm×4 mm.

Numerical data on the optical members that form the reimaging optical system of Example 3 will be given later.

Parameters for the conditions in the example here are given just below.

| Parameters | Symbol | Unit | Value |
|---|---|---|---|
| Image guide's diameter | D | [mm] | 0.8 |
| Optical transverse magnification | β | | −4.003 |
| Minor-axis direction length of the imaging device | V | [mm] | 4 |
| Focal length of the front unit | $f_F$ | [mm] | 5.07 |
| Focal length of the whole system | F | [mm] | 2.434 |
| Focal length of the positive lens in the second lens group | $f_{2P}$ | [mm] | 6.596 |
| Focal length of the rear unit | $f_B$ | [mm] | −238.18 |

In the example here, no quartz filter is located. For this reason, dots of the image guide may be seen; however, it is not impossible to use the reimaging optical system according to the example here.

EXAMPLE 4

Figure 4:
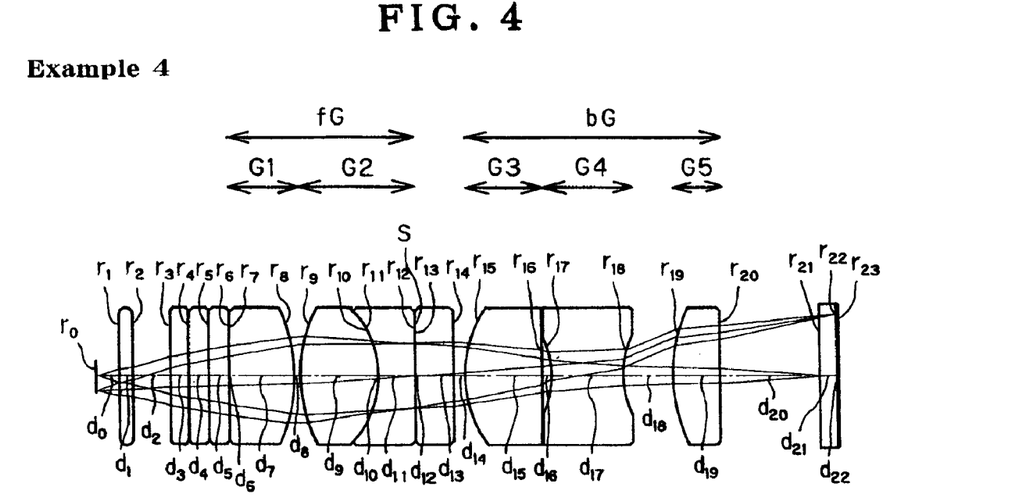
FIG. 4 is illustrative in lens arrangement of the reimaging optical system according to Example 4 of the invention.
Figure 9:
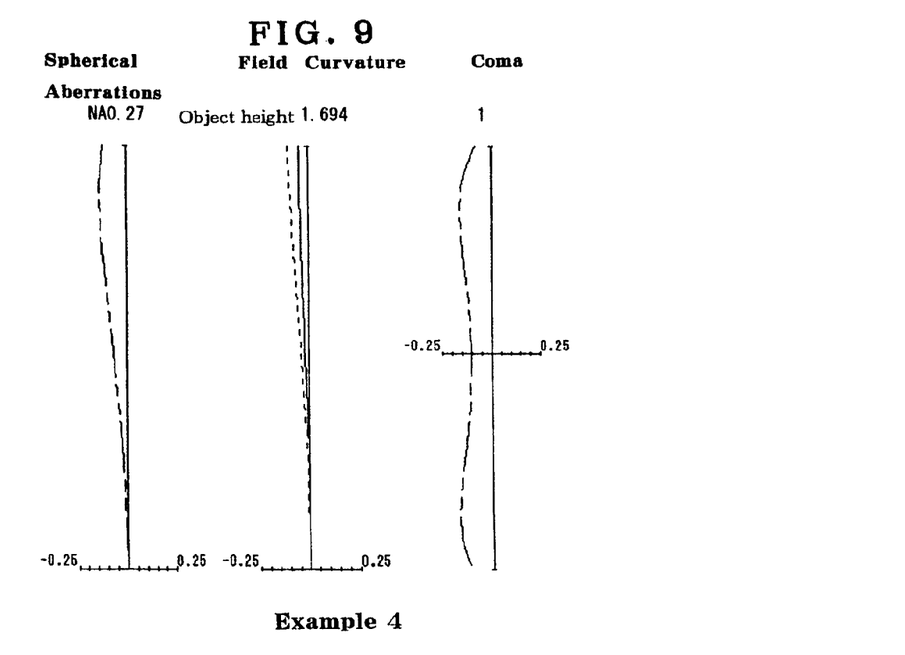
FIG. 9 is an aberration diagram for Example 4.

FIG. 4 is illustrative in lens arrangement of the reimaging optical system according to Example 4 of the invention, and FIG. 9 is an aberration diagram for Example 4. As shown in FIG. 4, the reimaging optical system here is built up of a front unit fG located on the object side of a stop S and a rear unit bG located on the image side of the stop S. The front unit fG is made up of a plano-convex positive lens convex on its image side and a cemented lens of a double-convex positive lens and a negative lens concave on its object side; the plano-convex positive lens forms the first group G1 and the cemented lens of a double-convex positive lens and a negative lens concave on its object side forms the second group G2. The rear unit bG is made up of a convex-plano positive lens convex on its object side, a double-concave negative lens and a convex-plano positive lens convex on its object side; the convex-plano positive lens located on the object side forms the third group G3, the double-concave negative lens forms the fourth group G4, and the convex-plano positive lens located on the image side forms the fifth group G5. Thus, the lens arrangement here comprises five groups or six lenses. A triplet optical low-pass filter is located on the object side of the front unit fG, and the effective imaging range of the imaging device is supposed to be 5.77 mm×4.34 mm. As in Example 2, an infrared cut filter is located just after the stop S.

Numerical data on the optical members that form the reimaging optical system of Example 4 will be given later.

Parameters for the conditions in the example here are given just below.

| Parameters | Symbol | Unit | Value |
|---|---|---|---|
| Image guide's diameter | D | [mm] | 0.8 |
| Optical transverse magnification | β | | −4.194 |
| Minor-axis direction length of the imaging device | V | [mm] | 4.34 |
| Focal length of the front unit | $f_F$ | [mm] | 2.984 |
| Focal length of the whole system | F | [mm] | 2.128 |
| Focal length of the positive lens in the second lens group | $f_{2P}$ | [mm] | 2.506 |
| Focal length of the rear unit | $f_B$ | [mm] | −18.022 |

EXAMPLE 5

Figure 5:
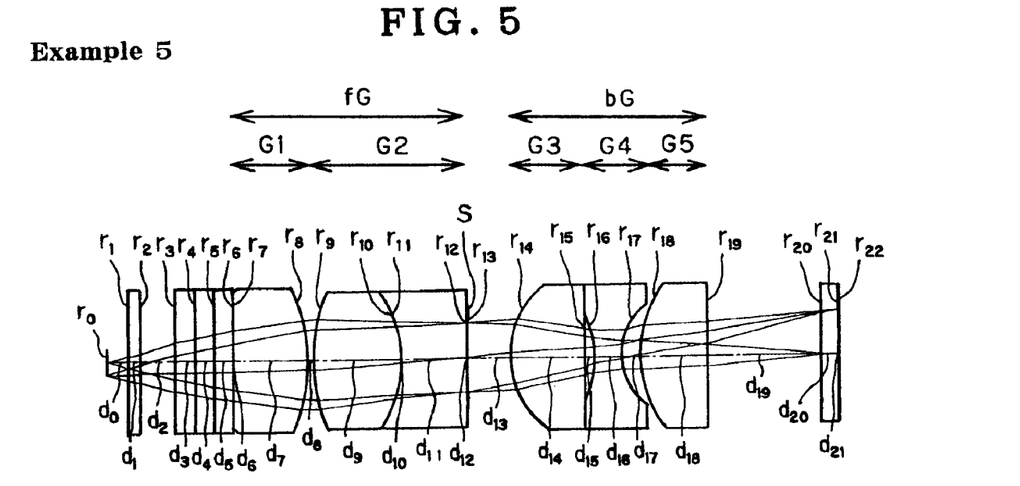
FIG. 5 is illustrative in lens arrangement of the reimaging optical system according to Example 5 of the invention.
Figure 10:
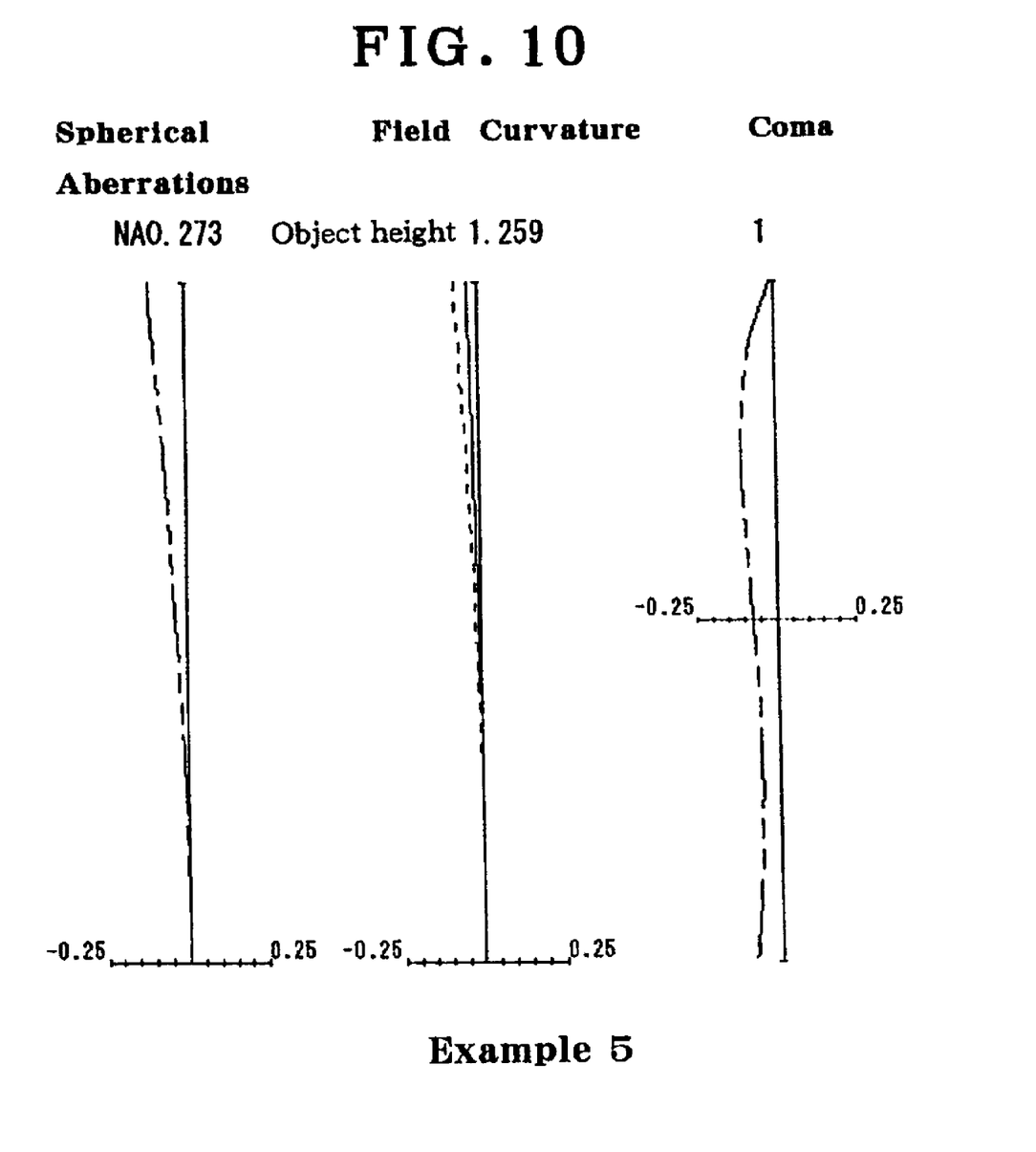
FIG. 10 is an aberration diagram for Example 5.

FIG. 5 is illustrative in lens arrangement of the reimaging optical system according to Example 5 of the invention, and FIG. 10 is an aberration diagram for Example 5. As shown in FIG. 5, the front unit fG is made up of a plano-convex positive lens convex on its image side and a cemented lens of a double-convex positive lens and a negative lens concave on its object side; the plano-convex positive lens forms the first group G1, and the cemented lens of a double-convex positive lens and a negative lens concave on its object side forms the second group G2. The rear unit bG is made up of a convex-plano positive lens convex on its object side, a double-concave negative lens, and a convex-plano positive lens convex on its object side; the convex-plano positive lens located on the object side forms the third group G3, the double-concave negative lens forms the fourth group G4, and the convex-plano positive lens located on the image side forms the fifth group G5. Thus, the lens arrangement here comprises five groups or six lenses. A triplet optical low-pass filter is located on the object side of the front unit fG, and the effective imaging range of the imaging device is supposed to be 5.33 mm×4 mm.

Numerical data on the optical members that form the reimaging optical system of Example 5 will be given later.

Parameters for the conditions in the example here are given just below.

| Parameters | Symbol | Unit | Value |
|---|---|---|---|
| Image guide's diameter | D | [mm] | 0.8 |
| Optical transverse magnification | β | | −3.113 |
| Minor-axis direction length of the imaging device | V | [mm] | 4 |
| Focal length of the front unit | $f_F$ | [mm] | 3.513 |
| Focal length of the whole system | F | [mm] | 2.320 |
| Focal length of the positive lens in the second lens group | $f_{2P}$ | [mm] | 3.230 |
| Focal length of the rear unit | $f_B$ | [mm] | 28.699 |

EXAMPLE 1

| No | r | d | ne | νe |
|---|---|---|---|---|
| 0 (object plane) | ∞ | 0.6 | 1 | |
| 1 | ∞ | 0.4 | 1.51825 | 63.93 |
| 2 | ∞ | 1 | 1 | |
| 3 | ∞ | 0.56 | 1.55098 | 45.49 |
| 4 | ∞ | 0.56 | 1.55098 | 45.49 |
| 5 | ∞ | 0.56 | 1.55098 | 45.49 |
| 6 | ∞ | 0.03 | 1 | |
| 7 | ∞ | 3 | 1.88815 | 40.52 |
| 8 | −6.353 | 0.2 | 1 | |
| 9 | ∞ | 1.5 | 1.51825 | 63.93 |
| 10 | −12.304 | 0.2 | 1 | |
| 11 | 9.374 | 3 | 1.73234 | 54.45 |
| 12 | −3.375 | 0.01 | 1.51193 | 62.74 |
| 13 | −3.375 | 1.5 | 1.81264 | 25.22 |
| 14 | ∞ | 0.03 | 1 | |
| 15 (Stop) | ∞ | 0.97 | 1 | |
| 16 | 7.0653 | 3.437 | 1.73234 | 54.45 |
| 17 | ∞ | 3.122 | 1 | |
| 18 | −2.2718 | 0.9 | 1.83945 | 42.47 |
| 19 | 5.8442 | 0.01 | 1.51193 | 62.74 |
| 20 | 5.8442 | 3.143 | 1.85504 | 23.59 |
| 21 | −6.3327 | 2.995 | 1 | |
| 22 | ∞ | 2 | 1.51825 | 63.93 |
| 23 | ∞ | 0.01 | 1.51193 | 62.74 |
| 24 | ∞ | 0.5 | 1.50186 | 63.89 |
| 25 | ∞ | 0.02 | 1.52197 | 62.74 |
| 26 | ∞ | 0.37 | 1 | |
| 27 (Image plane) | ∞ | | | |

EXAMPLE 2

| No | r | d | ne | νe |
|---|---|---|---|---|
| 0 (object plane) | ∞ | 1.4 | 1 | |
| 1 | ∞ | 0.63 | 1.55098 | 45.49 |
| 2 | ∞ | 0.63 | 1.55098 | 45.49 |
| 3 | ∞ | 0.63 | 1.55098 | 45.49 |
| 4 | ∞ | 0.35 | 1 | |
| 5 | −6.881 | 2 | 1.88815 | 40.52 |
| 6 | −4.4 | 0.3 | 1 | |
| 7 | ∞ | 2.8 | 1.51825 | 63.93 |
| 8 | 316.464 | 0.3 | 1 | |
| 9 | 7.825 | 2.6 | 1.73234 | 54.45 |
| 10 | −4.517 | 0.01 | 1.51193 | 62.74 |
| 11 | −4.517 | 2.6 | 1.81264 | 25.22 |
| 12 (Stop) | ∞ | 0.03 | 1 | |
| 13 | ∞ | 1 | 1.51564 | 74.74 |
| 14 | ∞ | 2.5 | 1 | |
| 15 | 15.022 | 3.5 | 1.73234 | 54.45 |
| 16 | ∞ | 2 | 1 | |
| 17 | −2.167 | 2.2 | 1.83945 | 42.47 |
| 18 | 5.353 | 0.01 | 1.51193 | 62.74 |
| 19 | 5.353 | 2.7 | 1.81264 | 25.22 |
| 20 | −5.353 | 1.6 | 1 | |
| 21 | ∞ | 0.5 | 1.50186 | 63.85 |
| 22 | ∞ | 0.02 | 1.52197 | 62.74 |
| 23 (Image plane) | ∞ | | | |

EXAMPLE 3

| No | r | d | ne | ve |
|---|---|---|---|---|
| 0 (object plane) | ∞ | 3.5 | 1 | |
| 1 | −5.934 | 2 | 1.88815 | 40.52 |
| 2 | −4.6223 | 0.3 | 1 | |
| 3 | ∞ | 1.7 | 1.51825 | 63.93 |
| 4 | −9.228 | 0.3 | 1 | |
| 5 | 9.2904 | 3 | 1.73234 | 54.45 |
| 6 | −8.6884 | 0.01 | 1.51193 | 62.74 |
| 7 | −8.6884 | 2 | 1.93429 | 18.74 |
| 8 | ∞ | 0.03 | 1 | |
| 9 (Stop) | ∞ | 2.9 | 1 | |
| 10 | 5.7603 | 2.5 | 1.73234 | 54.45 |
| 11 | ∞ | 1 | 1 | |
| 12 | −9.1702 | 1.95 | 1.81264 | 25.22 |
| 13 | −9.2872 | 1.5 | 1 | |
| 14 | −2.4149 | 1 | 1.83945 | 42.47 |
| 15 | 14.1445 | 0.01 | 1.51193 | 62.74 |
| 16 | 14.1445 | 2.5 | 1.81264 | 25.22 |
| 17 | −14.1445 | 4 | 1 | |
| 18 | ∞ | 0.5 | 1.51825 | 63.93 |
| 19 | ∞ | 0.35 | 1 | |
| 20 (Image plane) | ∞ | | | |

EXAMPLE 4

| No | r | d | ne | ve |
|---|---|---|---|---|
| 0 (object plane) | ∞ | 0.6 | 1 | |
| 1 | ∞ | 0.4 | 1.51825 | 63.93 |
| 2 | ∞ | 1 | 1 | |
| 3 | ∞ | 0.56 | 1.55098 | 45.49 |
| 4 | ∞ | 0.56 | 1.55098 | 45.49 |
| 5 | ∞ | 0.56 | 1.55098 | 45.49 |
| 6 | ∞ | 0.03 | 1 | |
| 7 | ∞ | 1.7 | 1.88815 | 40.52 |
| 8 | −4.827 | 0.2 | 1 | |
| 9 | 4.218 | 2.2 | 1.73234 | 54.45 |
| 10 | −2.532 | 0.01 | 1.51193 | 62.74 |
| 11 | −2.532 | 1 | 1.81264 | 25.22 |
| 12 (Stop) | ∞ | 0.03 | 1 | |
| 13 | ∞ | 1 | 1.51564 | 74.74 |
| 14 | ∞ | 0.3 | 1 | |
| 15 | 3.254 | 2.1 | 1.75844 | 52.08 |
| 16 | ∞ | 0.3 | 1 | |
| 17 | −2.339 | 2 | 1.83945 | 42.47 |
| 18 | 2.339 | 1.44 | 1 | |
| 19 | 4.7195 | 1.3 | 1.85504 | 23.59 |
| 20 | ∞ | 2.78 | 1 | |
| 21 | ∞ | 0.5 | 1.50186 | 63.85 |
| 22 | ∞ | 0.02 | 1.52197 | 62.74 |
| 23 (Image plane) | ∞ | | | |

EXAMPLE 5

| No | r | d | ne | ve |
|---|---|---|---|---|
| 0 (object plane) | ∞ | 0.6 | 1 | |
| 1 | ∞ | 0.4 | 1.51825 | 63.93 |
| 2 | ∞ | 1 | 1 | |
| 3 | ∞ | 0.56 | 1.55098 | 45.49 |
| 4 | ∞ | 0.56 | 1.55098 | 45.49 |
| 5 | ∞ | 0.56 | 1.55098 | 45.49 |
| 6 | ∞ | 0.03 | 1 | |
| 7 | ∞ | 2.1 | 1.88815 | 40.52 |
| 8 | −5.268 | 0.2 | 1 | |
| 9 | 5.268 | 2.6 | 1.73234 | 54.45 |
| 10 | −3.398 | 0.01 | 1.51193 | 62.74 |
| 11 | −3.398 | 1.9 | 1.85504 | 23.59 |
| 12 | ∞ | 0.03 | 1 | |
| 13 (Stop) | ∞ | 1.2 | 1 | |
| 14 | 2.665 | 2.2 | 1.73234 | 54.45 |
| 15 | ∞ | 0.3 | 1 | |
| 16 | −3.002 | 0.8 | 1.83945 | 42.47 |
| 17 | 1.883 | 0.5 | 1 | |
| 18 | 3.281 | 2 | 1.85504 | 23.59 |
| 19 | ∞ | 3.4 | 1 | |
| 20 | ∞ | 0.5 | 1.50186 | 63.85 |
| 21 | ∞ | 0.02 | 1.52197 | 62.74 |
| 22 (Image plane) | ∞ | | | |

Set out below are the values of conditions (1) to (4), (2)' and (3)' in Examples 1 to 5.

| Condition | Ex. 1 | Ex. 2 | Ex. 3 | Ex. 4 | Ex. 5 |
|---|---|---|---|---|---|
| (1) | 0.763 | 0.77 | 0.801 | 0.773 | 0.623 |
| (2) + (2)' | 1.327 | 1.028 | 2.083 | 1.402 | 1.514 |
| (3) + (3)' | 1.14 | 1.090 | 2.71 | 1.177 | 1.392 |
| (4) | 15.069 | 6.598 | 46.978 | 6.04 | 8.169 |

From the aforesaid table, it is found that with the reimaging optical system of each example, the images by the image fibers are formed on the solid-state imaging device with sizes of 0.623 to 0.801 relative to the minor-axis direction length of the imaging area.

Figure 12:
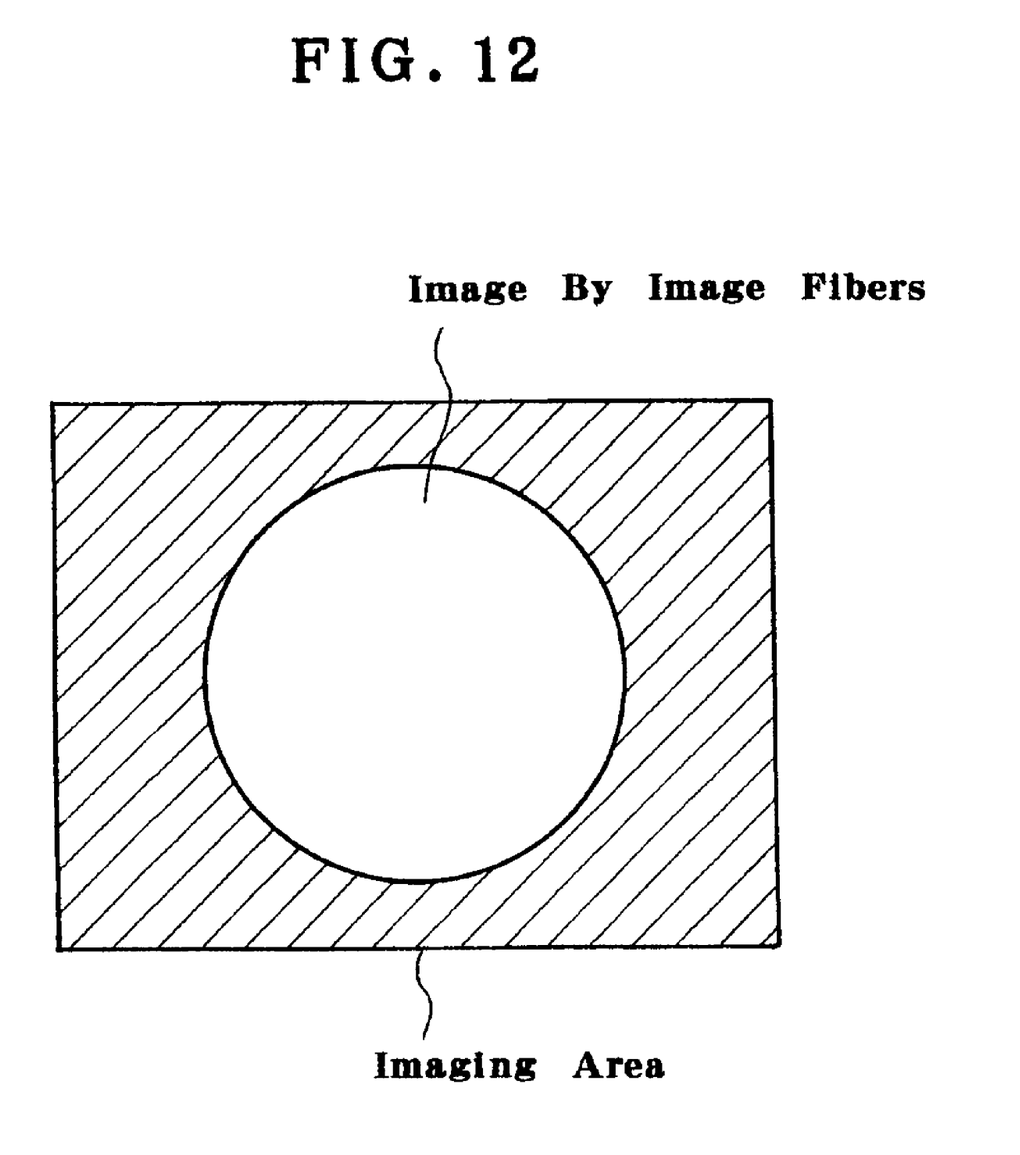
FIG. 12 is illustrative of images on the end face of a bundle of image guide fibers vs. the imaging plane of a CCD in the case where the reimaging optical system of Example 1 is used.

FIG. 12 is illustrative of what relations an image on the end face of the bundle of image guide fibers has to the imaging plane of the solid-state imaging device in the case where the reimaging optical system of Example 1 is used. The image of this size on the end face of the bundle of image guide fibers has a magnification that does not interfere with observation, even when it is observed as such. Also, even when the image is electrically enlarged to 1.25 or 1.6 times as large, it can be displayed 100% relative to the minor-axis direction length of the imaging area; image quality deterioration is limited to within such a degree as not to interfere with observation.

From the aforesaid table and the aberration diagrams, it is found that various aberrations inclusive of spherical aberrations can be well reduced by the satisfaction of the aforesaid conditions.

Figure 13A:
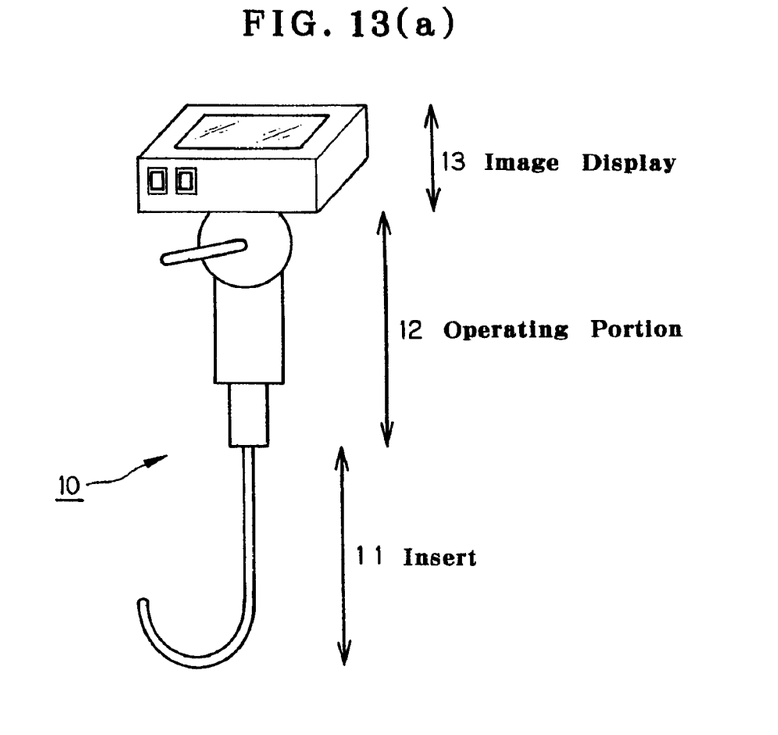
FIG. 13 is illustrative of one example of the endoscope using the inventive reimaging optical system.
Figure 13B:
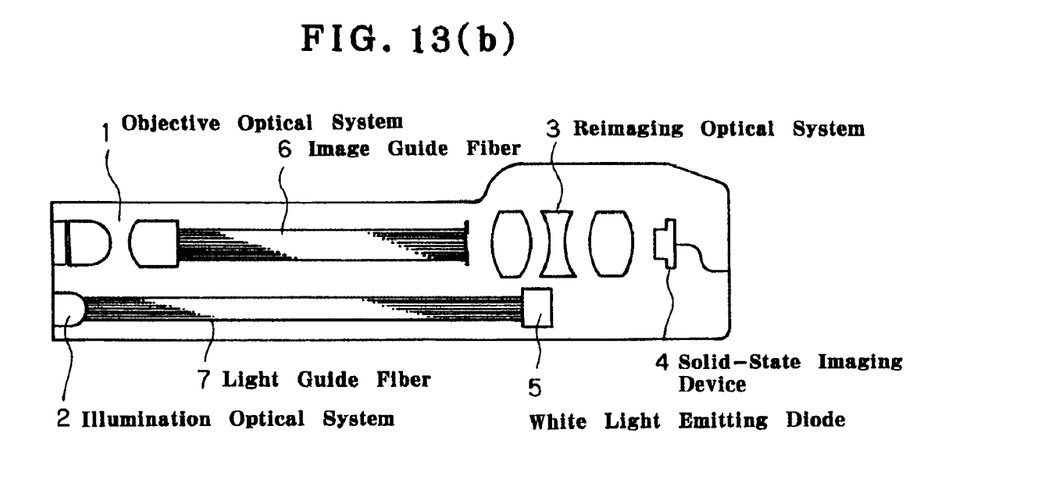
Figure 14:
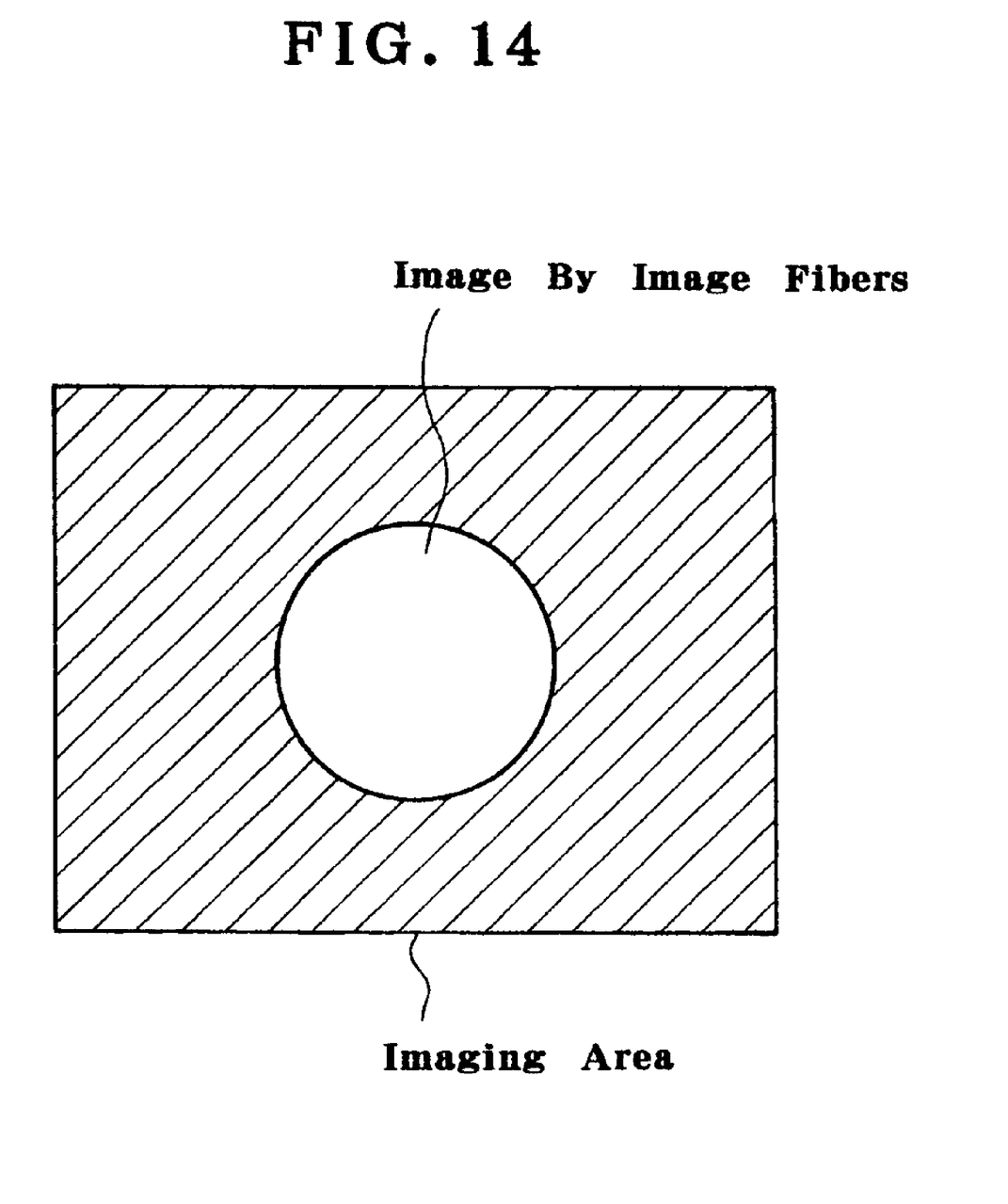
FIG. 14 is illustrative of images on the end face of a bundle of image guide fibers vs. the imaging plane of a CCD in the case where a conventional reimaging optical system is used.

The reimaging optical system of the invention has been described with reference to some specific examples. Such an inventive reimaging optical system may be used to set up an endoscope. FIG. 13 is illustrative of one example of the endoscope using the inventive reimaging optical system: FIG. 13(a) is illustrative of the whole endoscope, and FIG. 13(b) is illustrative in enlarged section of the endoscope from an insert 11 to an operating portion 12. An endoscope 10 here comprises an insert 11 having an objective optical system 1 and an illumination optical system 2, a reimaging optical system 3 according to any one of Examples 1-5, a solid-state imaging device 4 located on the image plane of the reimaging optical system 3, an operating portion 12 having a light source comprising a white light emitting diode 5, and an image display device 13 integral with the operating portion 12. And an image guide fiber 6 is interposed between the objective optical system 1 and the reimaging optical system 3, and a light guide fiber 7 is interposed between the white light emitting diode 5 and the illumination optical system 2. By the image guide fiber 6 and light guide fiber 7, the insert 11 is linked to the operating portion 12. It is thus possible to provide an endoscope that dispenses with any conventional heavy, bulky endoscope system, and is improved in carryability.

I claim:

1. A reimaging optical system adapted to re-form an image by an image guide on a solid-state imaging device having a diagonal length of 6.5 mm or longer, characterized by satisfying the following condition:

$$0.6 < (D \times \beta)/V \tag{1}$$

where D is a diameter of said image guide, $\beta$ is an optical transverse magnification of said reimaging optical system, and V in mm is a minor axis direction length of an imaging area of said solid-state imaging device.

2. The reimaging optical system according to claim 1, characterized by comprising a front unit, a stop and a rear unit, and satisfying the following condition (2):

$$1 < f_F/F \tag{2}$$

where $f_F$ is a focal length of the front unit, and F is a focal length of the whole reimaging optical system.

3. The reimaging optical system according to claim 2, characterized in that said front unit comprises a first lens group including at least one positive single lens and a second lens group including a cemented lens of a positive lens and a negative lens, and satisfies the following condition:

$$0.9 < f_{2F}/F \tag{3}$$

where $f_{2F}$ is a focal length of the positive lens in the second lens group.

4. The reimaging optical system according to claim 1, characterized by comprising a front unit, a stop and a rear unit, and satisfying the following condition:

$$6 < f_B/f_F \tag{2}$$

where $f_F$ is a focal length of the front unit, and $f_B$ is focal length of the rear unit.

5. The reimaging optical system according to claim 1, characterized in that an optical low-pass filter is located of an image side of said image guide.

6. An endoscope, characterized by comprising an objective lens located at an end of the endoscope, an image guide for guiding an object image formed by said objective lens, and a reimaging optical system adapted to re-form the object image guided by said image guide onto a solid-state imaging device having a diagonal length of 6.5 mm or longer, wherein the reimaging optical system according to claim 1 is used as said reimaging optical system.

7. The endoscope according to claim 6, characterized by further comprising an illumination means that includes a white light emitting diode without recourse to any color correction filter.

8. The endoscope according to claim 6, characterized by further comprising a display means for displaying an image based on electric signals from said solid-state imaging device.

* * * * *

UNITED STATES PATENT AND TRADEMARK OFFICE
CERTIFICATE OF CORRECTION

| | | |
|---|---|---|
| PATENT NO. | : 8,139,296 B2 | |
| APPLICATION NO. | : 12/368954 | |
| DATED | : March 20, 2012 | |
| INVENTOR(S) | : Ito | |

It is certified that error appears in the above-identified patent and that said Letters Patent is hereby corrected as shown below:

Abstract
Line 1, change "an reimaging" to -- a reimaging --;

Column 2
Lines 43, change the equation to:
   -- $f_{2p}/F<3$        (3') --;

Column 2
Lines 66-67, change "stand very conspicuous." to
   -- stand out very conspicuously. --;

Column 3
Line 29, change "spectra from the light emitting diode contain"
   to -- spectrum from the light emitting diode contains --;

Column 8
Example 2, surface No. 8, change the r value from "316.464"
   to -- -6.464 --;
Example 2, surface No. 12, change "12" to -- 12 (Stop) --; and
   on the line below, delete "(Stop)";

Column 9
Example 3, surface No. 9, change "9" to -- 9 (Stop) --; and
   on the line below, delete "(Stop)";

Column 9
Example 4, surface No. 12, change "12" to -- 12 (Stop) --; and
   on the line below, delete "(Stop)";

Signed and Sealed this
Tenth Day of July, 2012

David J. Kappos
*Director of the United States Patent and Trademark Office*

In claim 1
Line 5, change "$0.6<(D\times\beta)/V \quad (1)$" to
-- $0.6<(D\times|\beta|)/V \quad (1)$ --; and In claim 5
Line 2, change "is located of an" to -- is located on an --.

UNITED STATES PATENT AND TRADEMARK OFFICE
CERTIFICATE OF CORRECTION

| | |
|---|---|
| PATENT NO. | : 8,139,296 B2 |
| APPLICATION NO. | : 12/368954 |
| DATED | : March 20, 2012 |
| INVENTOR(S) | : Ito |

It is certified that error appears in the above-identified patent and that said Letters Patent is hereby corrected as shown below:

Title Page, Item (57) Abstract
Line 1, change "an reimaging" to -- a reimaging --;

Column 2
Lines 43, change the equation to:
 -- $f_{2p}/F<3$      (3') --;

Column 2
Lines 66-67, change "stand very conspicuous." to
 -- stand out very conspicuously. --;

Column 3
Line 29, change "spectra from the light emitting diode contain"
 to -- spectrum from the light emitting diode contains --;

Column 8
Example 2, surface No. 8, change the r value from "316.464"
 to -- -6.464 --;
Example 2, surface No. 12, change "12" to -- 12 (Stop) --; and
 on the line below, delete "(Stop)";

Column 9
Example 3, surface No. 9, change "9" to -- 9 (Stop) --; and
 on the line below, delete "(Stop)";

This certificate supersedes the Certificate of Correction issued July 10, 2012.

Signed and Sealed this
Fourteenth Day of August, 2012

David J. Kappos
*Director of the United States Patent and Trademark Office*

CERTIFICATE OF CORRECTION (continued)
U.S. Pat. No. 8,139,296 B2

Column 9
Example 4, surface No. 12, change "12" to -- 12 (Stop) --; and
    on the line below, delete "(Stop)";

Column 11
Line 20 (Claim 1, Line 5) change "$0.6<(D\times\beta)/V$ (1)" to
    -- $0.6<(D\times|\beta|)/V$     (1) --; and Column 12
Line 16 (Claim 5, Line 2) change "is located of an" to -- is located on an --.